(12) United States Patent
Fisher

(10) Patent No.: US 6,872,185 B2
(45) Date of Patent: Mar. 29, 2005

(54) DUAL ACTION ASPIRATION BIOPSY NEEDLE

(75) Inventor: John S. Fisher, Belleair, FL (US)

(73) Assignee: Biopsy Sciences, LLC, Clearwater, FL (US)

( * ) Notice: Subject to any disclaimer, the term of this patent is extended or adjusted under 35 U.S.C. 154(b) by 0 days.

(21) Appl. No.: 10/708,710

(22) Filed: Mar. 19, 2004

(65) Prior Publication Data

US 2004/0167433 A1 Aug. 26, 2004

Related U.S. Application Data

(60) Division of application No. 10/065,155, filed on Sep. 23, 2002, now Pat. No. 6,709,408, which is a continuation-in-part of application No. 09/682,252, filed on Aug. 9, 2001, now abandoned.

(51) Int. Cl.[7] .............................................. A61B 10/00
(52) U.S. Cl. ...................... 600/570; 600/571; 600/562; 600/576; 606/160; 604/22
(58) Field of Search ......................... 600/562, 564–567, 600/570–573, 576, 582; 606/79, 160, 170, 171, 181, 184, 185; 604/22, 164.01, 44, 164.11, 264, 272

(56) References Cited

U.S. PATENT DOCUMENTS

| | | | | |
|---|---|---|---|---|
| 4,702,260 A | * | 10/1987 | Wang | 600/566 |
| 5,394,887 A | * | 3/1995 | Haaga | 600/567 |
| 5,560,373 A | * | 10/1996 | De Santis | 600/566 |
| 5,843,111 A | * | 12/1998 | Vijfvinkel | 606/171 |
| 5,957,864 A | * | 9/1999 | Oosterhof | 600/576 |

* cited by examiner

*Primary Examiner*—Charles Marmor
(74) *Attorney, Agent, or Firm*—Ronald E. Smith; Smith & Hopen, P.A.

(57) ABSTRACT

A biopsy needle scrapes tissue of cellular thickness from a lesion during repeated proximal-to-distal thrusts of the needle along its longitudinal axis of symmetry. A first sharp edge, formed by a beveled distal end of the needle, scrapes tissue during proximal-to-distal travel of the needle. A second sharp edge is provided by a transversely disposed slot formed in the needle near the first sharp edge. The second sharp edge also scrapes tissue during proximal-to-distal travel of the needle. The second sharp edge may be coincident with an exterior surface of the needle elevated with respect to the exterior surface, or recessed with respect to the exterior surface. Another embodiment includes a hinge for enabling pivotal movement of the second sharp edge.

2 Claims, 5 Drawing Sheets

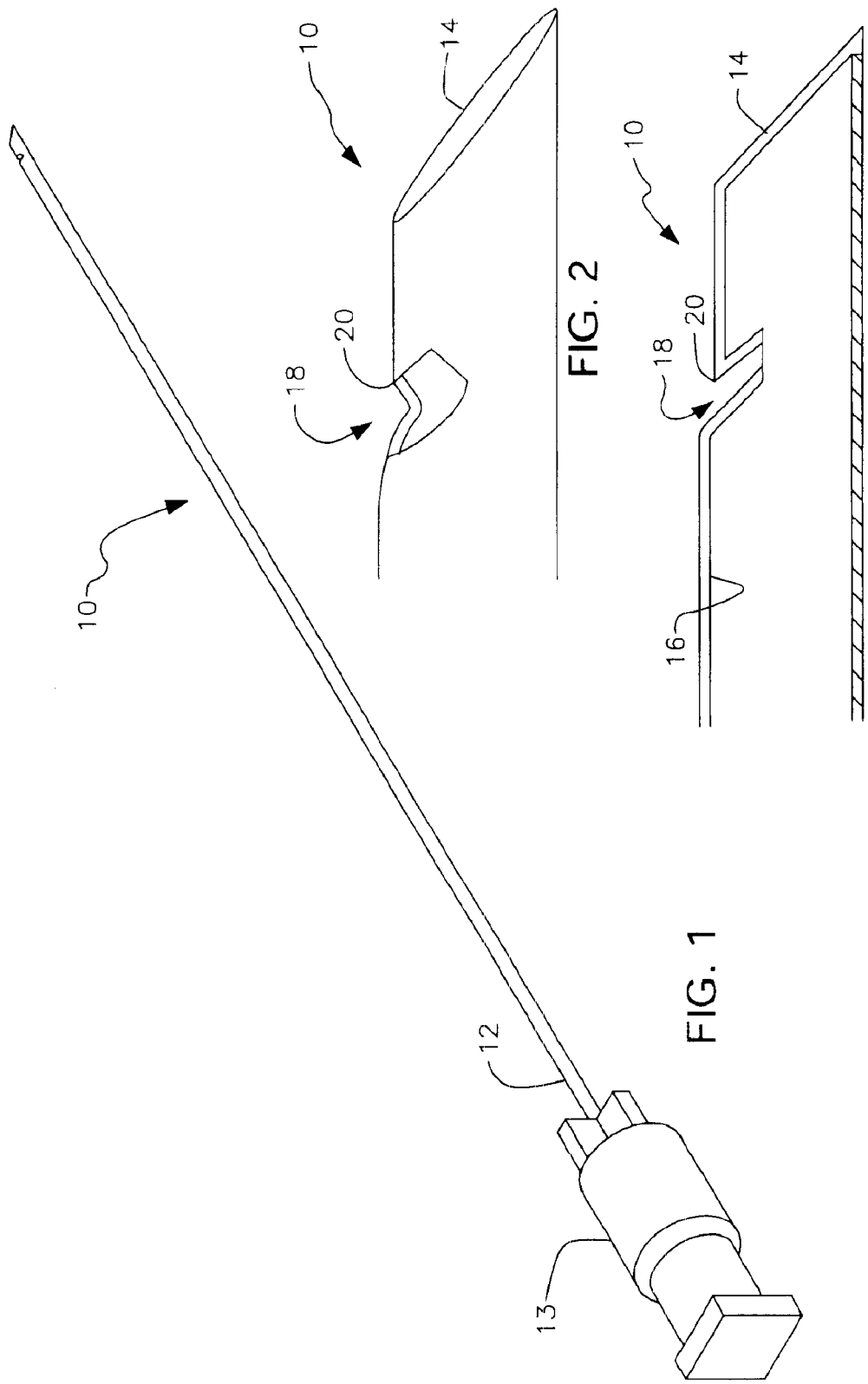

DUAL ACTION ASPIRATION BIOPSY NEEDLE

CROSS-REFERENCE TO RELATED DISCLOSURES

This disclosure is a divisional application claiming the benefit of the filing date of U.S. patent application entitled: "Dual Action Aspiration Biopsy Needle," by the same inventor, filed on Sep. 23, 2002, bearing Ser. No. 10/065,155 now U.S. Pat. No. 6,709,408 which is a continuation-in-part of U.S. patent application of the same title by the same inventor, filed Aug. 9, 2001, bearing Ser. No. 09/682,252, now abandoned.

BACKGROUND OF THE INVENTION

1. Field of the Invention

This invention relates, generally, to aspiration biopsy needles. More particularly, it relates to an aspiration biopsy needle having an enhanced cellular material collection capability.

2. Description of the Prior Art

There are three main types of biopsy procedures. In a first type, a conventional surgical incision is made and the patient's body is opened so that a surgeon may retrieve one or more large pieces of the tumor or lesion to be tested for malignancy. This type of biopsy is very invasive, expensive to perform, and requires a considerable recovery time. Inventive endeavors in the field have resulted in two improved procedures that substantially reduce the invasiveness of the biopsy procedure, as well as the expense of the procedure and the length of the recovery time.

The first improved procedure involves the cutting or shearing of one or more visible pieces of the tumor or lesion by a relatively large bore needle. This type of biopsy is known an a core tissue biopsy and is performed with a core tissue biopsy needle. The pieces of tissue are usually about one to three millimeters in length and are thus visible to the unaided eye. They cannot be immediately examined under a microscope because they are too thick for light to pass therethrough. Accordingly, they must first be sliced into a plurality of very thin slices by a tissue-slicing machine. After slicing, they are then stained with a tissue fixative e.g., formalin, glutaraldehyde, etc., and placed upon a microscope slide for diagnostic purposes. For a period of time sufficient to cause crosslinking of connective tissue proteins present in the tissue, the fixed tissue is sliced into thin sections approximately eight (8) microns thick, the tissue sections are mounted on slides and cell-selective histological stains are applied to stain the tissue prior to microscopic examination. This non-frozen tissue preparation technique typically requires twenty four to forty eight (24–48) hours to complete so the pathologist's diagnosis of the breast lesion may not be available until twenty four to seventy two (24–72) hours after the biopsy specimen was removed from the breast. Accordingly, histopathological examination and diagnosis of breast lesions may be much more time-consuming than the histopathological examination and diagnosis of other types of lesions.

The use of a core tissue biopsy needle thus represents a significant improvement over the more invasive surgical removal of tumor or lesion specimens. However, the need to slice the specimens causes a delay in providing the diagnosis, due to processing. Additionally, the diameter of core biopsy needles are typically larger than the diameter of fine needle aspiration (FNA) needles, thereby increasing the risk of procedure-related complications including bleeding, pneumothorax, and bile leakage. Moreover, the use of core biopsy needles necessitates the purchase and maintenance of tissue slicing machines. The material must be removed from the needle, deposited onto the machine, machine-sliced, removed from the machine after slicing, stained, and deposited onto a microscope slide.

One example of a core tissue biopsy needle is disclosed in U.S. Pat. No. 5,320,110 to Wang. The Wang structure has utility in performing a pleural tissue biopsy by cutting tissue samples of the parietal pleura. Wang teaches a two needle (tube-in-tube) system having a sharp edge to fix tissue while a second needle is advanced to shear off a piece of the tissue. The device does not rely solely on a vacuum to draw in material as in an FNA biopsy needle and tissue is sheared off in sizeable, visible pieces, i.e., not at the cellular level.

More particularly, in the Wang device, a hook engages the pleural tissue and an outer cannula is advanced to cut off the hooked piece of pleural tissue. This two needle system is designed to reduce the chances of a pneumothorax and thus represents a significant improvement over earlier biopsy techniques. However, the diameter of the Wang needle as described is about 4.5 mm, which is considerably larger than an FNA biopsy needle of the novel type disclosed herein which is typically no larger than 20–22 gauge. The Wang needle is not designed as a fine needle aspiration device but is designed to cut off pieces of lung pleura. A large diameter needle like the Wang device measuring about 4.5 mm in diameter is inappropriate for fine needle biopsy procedures due to the high risk of complications from a large tissue puncture including bleeding, pneumothorax and bile leakage.

The Wang structure includes a notch formed in a first side of the large bore needle and a hole in an opposite side thereof. The tissue to be cut extends into the notch and is sliced off when the outer needle or cannula is advanced as aforesaid. No such opposing hole can be provided in an FNA biopsy needle because such hole would allow the escape of cellular material when it is deposited directly from the syringe barrel onto a microscope slide in which the distal tip bevel and side notch must point in the same direction.

The distal tip of the Wang outer needle is not hollow and therefore no tissue cutting occurs at said distal tip. All tissue cutting occurs at the side of the Wang needle where the notch is positioned. Thus, the Wang needle collects relatively large samples in a knifing action, and performs no scraping action capable of collecting samples at the cellular level.

Neither Wang nor any other known two needle systems include both an open distal end and a port for cutting tissue nor is any core biopsy system capable of collecting samples of cellular thickness. It should also be observed that the Wang needle is attached to a syringe barrel and includes a pressure flap.

Other biopsy tools that collect large specimens include spring-loaded core biopsy guns. An example of a vacuum-assisted biopsy device is the Mammotome Biopsys® breast biopsy device.

The third technique is called fine needle aspiration (FNA) biopsy and is performed with an FNA biopsy needle. An FNA biopsy needle scrapes cells from the tumor or lesion that are so small as to be invisible to the unaided eye. Advantageously, the cellular material is already very thin when it is collected so there is no need to slice it to a thinner size prior to viewing it on a microscope slide because light can already pass through the thin cell layer. The cellular material is deposited onto a microscope slide directly from the FNA biopsy needle, stained, and viewed so that there is less time to the final biopsy report because the slicing machine and all of the handling steps necessitated thereby are eliminated. Trauma to the patient is greatly reduced because of smaller needle diameter and because cells are scraped instead of tissue being cut in thick pieces. Complication risk is also minimized or eliminated due to smaller nozzle diameters.

FNA biopsy needles collect samples by aspiration; a vacuum applied to the proximal end of a hollow needle pulls severed cellular material from the lesion into the lumen of the needle. The needle is then retracted from the soft tissue so that the cellular material in the lumen can be removed for analysis. If more samples of the lesion are needed, the biopsy needle is reintroduced into the lesion.

The primary distinction between an FNA biopsy needle and a core tissue biopsy needle is that the latter cuts or slices relatively large pieces of tissue from a lesion or tumor whereas the former scrapes cellular material from a lesion or tumor. By way of analogy, a core needle aspiration biopsy needle is like a knife that cuts slices of cheese and an FNA biopsy needle is like a cheese grater that scrapes small flakes of cheese.

Sometimes, however, the FNA biopsy procedure fails to collect a sample of sufficient size to enable definitive pathological analysis. When that happens, the physician must repeat the procedure, causing additional trauma to the body part undergoing biopsy and creating an additional risk of an adverse event.

The primary reason that conventional FNA biopsy needles are sometimes unable to collect sufficient cellular material is that the only cutting action occurs at the hollow distal tip of the needle. Thus, no scraping occurs during the retraction stroke of the needle, i.e., scraping occur only in the forward thrust.

Although FNA biopsy needles represent a significant improvement over more invasive procedures for performing biopsies on suspect lesions or tumors, there remains a need for an improved FNA biopsy needle that increases the amount of sample that may be recovered per entrance into the lesion with one needle insertion so that multiple insertions need not be performed to complete a biopsy procedure.

However, in view of the prior art considered as a whole at the time the present invention was made, it was not obvious to those of ordinary skill in the pertinent art how the standard FNA biopsy needle could be improved.

SUMMARY OF INVENTION

The longstanding but heretofore unfulfilled need for a biopsy needle having enhanced cellular material collection capability is now met by a new, useful, and nonobvious invention. The novel aspiration biopsy needle includes a single needle of elongate, hollow construction having a proximal end and a beveled distal end. The beveled distal end of the needle is open and therefore forms a first sharp edge adapted to scrape cellular material when the needle is inserted into tissue. The needle is displaced from a proximal position to a distal position during insertion. The needle has a uniform diameter along a substantial part of its extent. A slot is formed in the needle near the beveled distal end; the slot is transversely disposed relative to a longitudinal axis of the needle. The slot is also angled relative to a transverse axis of the needle such that a bottom of the slot is positioned distal to an opening of the slot. The opening of the slot includes a second sharp edge adapted to scrape tissue of cellular size when the needle is displaced from a distal position to a proximal position. The novel structure further includes conventional means for applying a vacuum to a proximal end of the needle so that cellular material removed by the first sharp edge during proximal-to-distal travel of the needle is pulled into a lumen of the needle and so that cellular material removed by the second sharp edge during distal-to-proximal travel of the needle is also pulled into the lumen. However, the novel structure also has utility when no vacuum means is employed, i.e., even if it is not affixed to a syringe barrel.

Accordingly, the cellular material is deposited from the lumen of the single FNA needle onto a slide for microscopic inspection in the absence of any need to slice said cellular material and to place said cellular material, following staining, into a formative to preserve the tissue.

In all embodiments, the slot has a circumferential extent of about one half the circumference of the needle.

In a first embodiment, the second sharp edge is coincident with the exterior surface of the needle.

In a second embodiment, the second sharp edge is raised with respect to the exterior surface of said needle, and in a third embodiment, the sharp edge is recessed with respect to said exterior surface.

In a fourth embodiment, the slot is also angled relative to a transverse axis of the needle such that a bottom of the slot is positioned proximal to an opening of the slot and the second sharp edge thereby created is coincident with the exterior surface of the needle.

In fifth and sixth embodiments, the second sharp edge of the fourth embodiment is elevated and recessed, respectively, relative to the exterior surface of the needle.

In a seventh embodiment, a first slot is formed in the needle as in the first embodiment and a second slot is formed in the needle as in the fourth embodiment. The first and second slots are longitudinally spaced apart from one an other.

In an eighth embodiment, a transversely disposed channel is formed in the needle and provides a second and a third sharp edge that are coincident with the exterior surface of the needle.

In ninth and tenth embodiments, the second and third sharp edges, respectively, are elevated with respect to the exterior surface of the needle and in eleventh and twelfth embodiments, the second and third sharp edges, respectively, are recessed with respect to said exterior surface.

In additional embodiments, the second sharp edge is mounted for pivotal movement about a transversely disposed hinge. The hinge enables the second sharp edge to open wider relative to its non-hinged position so that it may scrape off larger numbers of cellular material as the needle is displaced in a distal-to-proximal direction.

In still further embodiments, the third sharp edge is mounted for pivotal movement about a transversely disposed hinge and in additional embodiments, both the second and third sharp edges are so mounted.

A primary object of the invention is to provide a fine needle aspiration biopsy needle that collects a greater quantity of cellular material per needle insertion than conventional fine needle aspiration biopsy needles.

A closely related object is to accomplish the foregoing object by making a structural change to an existing FNA biopsy needle so that physicians will have a sense of familiarity when employing the improved needle.

A more specific object is to provide an FNA biopsy needle capable of collecting cellular material as the needle is reciprocated along its longitudinal axis at a tissue collection site.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is a perspective view of a first embodiment of the novel aspiration biopsy needle;

FIG. 2 is an enlarged perspective view of the distal end of the needle of said first embodiment;

FIG. 3 is an enlarged longitudinal sectional view of the parts depicted in FIG. 2;

DETAILED DESCRIPTION

Figure 4:
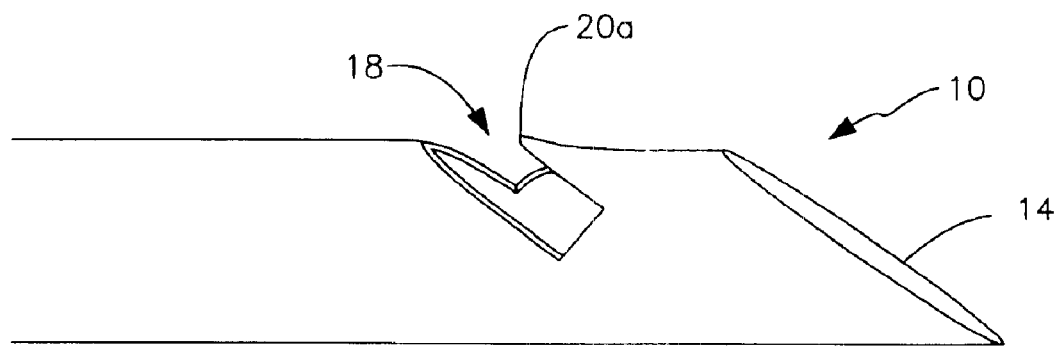
FIG. 4 is an enlarged perspective view of the distal end of a second embodiment.

Referring now to FIGS. 1–3, it will there be seen that the reference numeral 10 denotes a first illustrative embodiment of the present invention.

The proximal end 12 of aspiration biopsy needle 10 is mounted in a LUER LOK® adapter 13 or equivalent structure to which a vacuum is applied from a remote source of negative pressure, not shown, when the leading or distal end 14 of said needle is inserted into a suspect lesion in soft tissue. The sharp leading end 14 is beveled in a well-known way to form a first sharp edge that scrapes cellular material from the lesion as it travels therethrough in a proximal-to-distal direction.

A vacuum applied to adapter 13 pulls cellular material severed from the lesion into lumen 16 of the needle. The well-known prior art procedure ends at this point, i.e., the needle having a sample of the lesion in its lumen is retracted from the soft tissue and the sample is delivered to a lab for analysis. Additional sample-taking requires additional insertions of the needle into the lesion.

A first innovation of this invention includes slot 18 formed in needle 10, near first sharp edge 14 thereof. Slot 18 is transversely disposed relative to a longitudinal axis of the needle. A lower end or bottom of the slot is distal to the open upper end thereof. A second sharp edge 20 is formed at the distal edge of the upper end of the slot. Accordingly, second sharp edge 20 scrapes cellular material from a lesion when the needle is retracted, i.e., when the needle is displaced along its longitudinal axis in a distal-to-proximal direction.

It should therefore be understood that a physician may reciprocate needle 10 along its longitudinal axis, collecting cells of a suspect lesion that are scraped off by the first sharp edge 14 during the proximal-to-distal portion of each reciprocation, and collecting cellular aspirate of said lesion that are scraped by second sharp edge 20 during the distal-to-proximal portion of each reciprocation. Thus, the chances of collecting a quantity of lesion that is sufficient for analysis is greatly enhanced by the provision of second sharp edge 20.

The circumferential extent of slot 18 is approximately equal to half of the circumference of needle 10, but that structural feature of slot 18 is not critical to this invention; the circumferential extent of said slot could be more or less than that described and depicted.

As perhaps best depicted in FIG. 3, second sharp edge 20 is coincident or flush with the exterior surface of needle 10 in this first embodiment.

Figure 5:
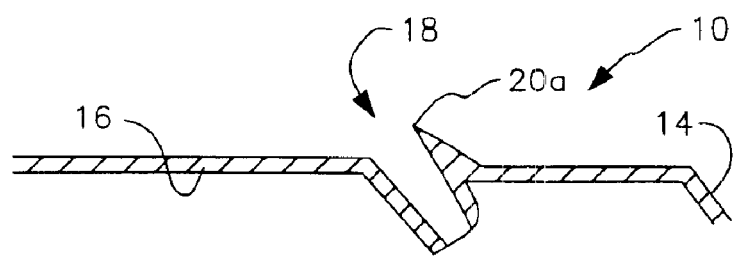
FIG. 5 is an enlarged longitudinal sectional view of the parts depicted in FIG. 4.

FIG. 4 provides a perspective view of a second embodiment of needle 10 where second sharp edge 20a is elevated with respect to the exterior surface of needle 10 and FIG. 5 provides a longitudinal sectional view of said second embodiment. The protrusion of second sharp edge 20a above the exterior surface of the needle ensures that the cellular material collected when using this second embodiment should be greater than the amount of cellular material collected when using the first embodiment.

Figure 6:
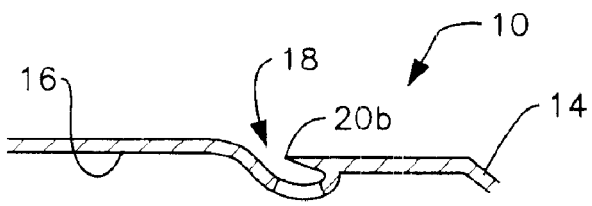
FIG. 6 is an enlarged longitudinal sectional view of a third embodiment.

FIG. 6 provides a longitudinal sectional view of a third embodiment where second sharp edge 20b is recessed with respect to said exterior surface. The lesion, not shown, is under compression as needle 10 penetrates it. Accordingly, an amount of tissue will enter into slot 18 and be scraped off during distal-to-proximal travel of needle 10, even though sharp edge 20b is recessed with respect to the exterior surface of the needle.

Figure 7:
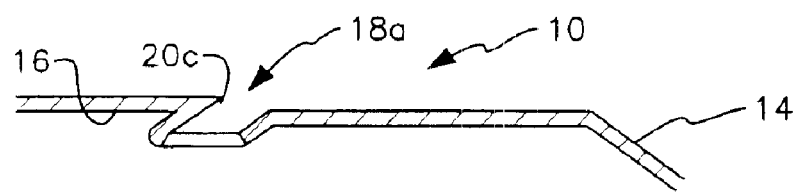
FIG. 7 is an enlarged longitudinal sectional view of a fourth embodiment.

FIG. 7 depicts a fourth embodiment where a slot 18a is formed transversely to the longitudinal axis of needle 10 as in the first embodiment, but the axis of symmetry of slot 18a is normal to the axis of symmetry of slot 18. In other words, the bottom of slot 18a is proximal to the open upper end of slot 18a. Accordingly, a third sharp edge, denoted 20c, is formed. Third sharp edge 20c is auxiliary to first sharp edge 14 in that said third sharp edge scrapes cellular material from a lesion during proximal-to-distal travel of needle 10.

Figure 8:
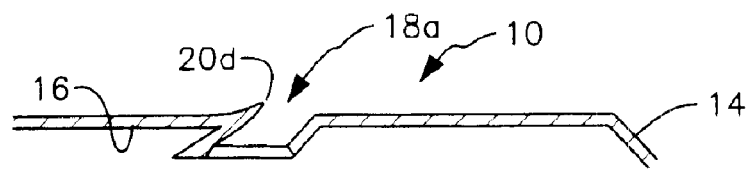
FIG. 8 is an enlarged longitudinal sectional view of a fifth embodiment.
Figure 9:
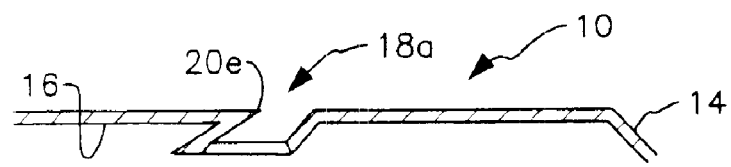
FIG. 9 is an enlarged longitudinal sectional view of a sixth embodiment.

FIGS. 8 and 9 depict fifth and sixth embodiments, respectively, where third sharp edges 20d and 20e are elevated and recessed, respectively, with respect to the exterior surface of needle 10.

Figure 10:
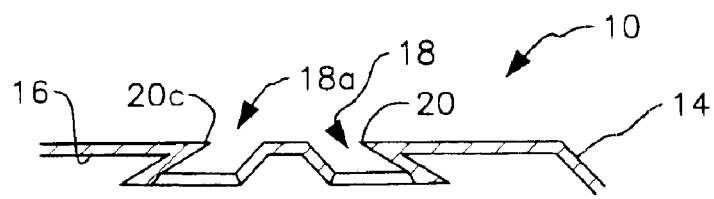
FIG. 10 is an enlarged longitudinal sectional view of a seventh embodiment.

A seventh embodiment, depicted in FIG. 10, includes first slot 18 of the first embodiment and second slot 18a of the fourth embodiment. The respective axes of symmetry of said slots are normal to one another and said slots 18 and 18a are longitudinally spaced apart from one another as depicted. In undepicted variations or permutations of this embodiment, second sharp edge 20 is elevated or recessed relative to the exterior surface of needle 10, as is third sharp edge 20c.

Figure 11:
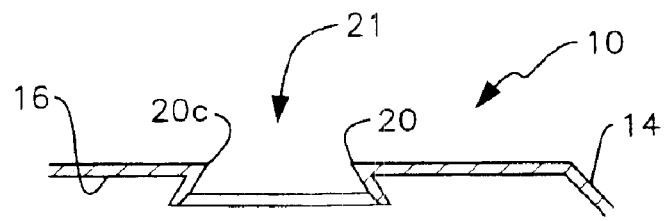
FIG. 11 is an enlarged longitudinal sectional view of a eighth embodiment.

FIG. 11 depicts an eighth embodiment. This embodiment, like the seventh, provides two auxiliary sharp edges to augment beveled edge 14. However, it provides a single transversely disposed channel as distinguished from two transversely disposed slots. Thus, instead of slot 18, transversely disposed channel 21 is formed in said needle 10. Channel 21 includes a pair of longitudinally spaced apart undercuts that respectively form second and third sharp edges 20 and 20c. Second sharp edge 20 performs in the same way as second sharp edge 20 of the first embodiment, i.e., it functions during distal-to-proximal travel of needle 10. Third sharp edge 20c, however, functions in the same way as third sharp edge 20c of the fourth embodiment, i.e., during proximal-to-distal travel. Thus, first sharp edge 14 and third sharp edge 20c function during proximal-to-distal travel, but the amount of cellular material scraped from the lesion during such sharp action may not be the same. This eighth embodiment is also similar to the seventh embodiment because second and third sharp edges 20, 20c are flush with the exterior surface of needle 10.

Figure 12:
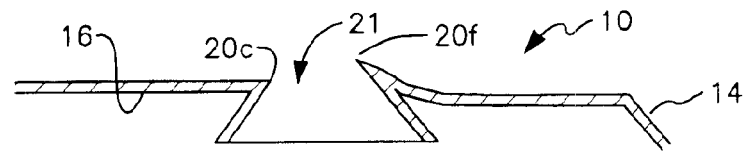
FIG. 12 is an enlarged sectional view of a ninth embodiment.
Figure 13:
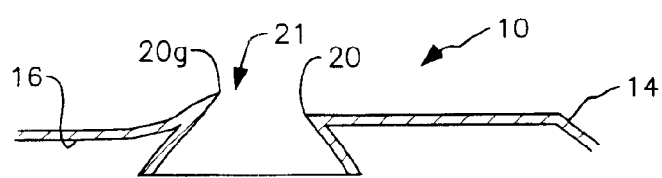
FIG. 13 is an enlarged sectional view of a tenth embodiment.

FIGS. 12 and 13 depict ninth and tenth embodiments, respectively, where second sharp edge 20f and third sharp edge 20g are elevated, respectively, with respect to the exterior surface of needle 10.

Figure 14:
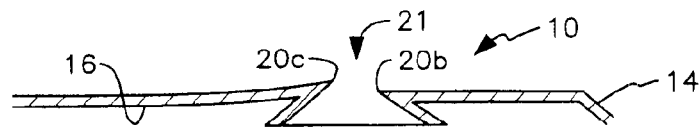
FIG. 14 is an enlarged sectional view of an eleventh embodiment.
Figure 15:
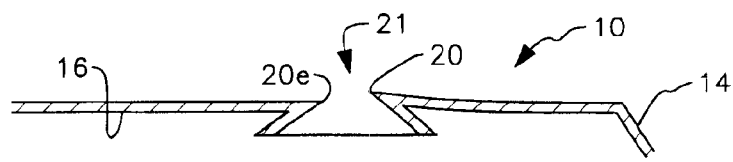
FIG. 15 is an enlarged sectional view of a twelfth embodiment.

FIGS. 14 and 15 depict eleventh and twelfth embodiments, respectively, where second sharp edge 20b and third sharp edge 20e are recessed, respectively, with respect to the exterior surface of needle 10.

Figure 16:
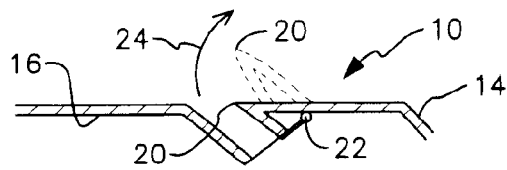
FIG. 16 is an enlarged sectional view of a thirteenth embodiment.

FIG. 16 provides a longitudinal sectional view where second sharp edge 20 is pivotally mounted by transversely disposed hinge means 22 so that second sharp edge 20 may open as indicated by arcuate directional arrow 24 to the position indicated in dotted lines to scrape larger numbers of cells from the suspect lesion during distal-to-proximal travel of the biopsy needle.

Second sharp edge 20 is biased against outward rotation. Various bias means such as different types of springs could be employed but the preferred bias means is a living hinge formed of nitenol or other suitable material. The hinge is held in its closed, FIG. 16 position when the needle is traveling in a proximal-to-distal direction i.e., as the needle is inserted, but opens due to frictional forces created by the lesion as depicted in dotted lines in FIG. 16 when the needle is retracted, i.e., when the needle is displaced in a distal-to-proximal direction.

Alternatively, a control means, not depicted, under the control of the physician, causes second sharp edge 20 to pivot about hinge means 22 in small incremental amounts so that the depth of the cellular aspirate taken from the lesion is controlled with precision.

It should be understood that, in addition to first sharp edge 20 of the first embodiment, sharp edges 20a, 20b, 20c, 20d, 20e, 20f, and 20g could also be provided in pivotal form and placed under the control of the control means.

Moreover, the cell-collection ability of each sharp edge 20, 20a, 20b, 20c, 20d, 20e, 20f, and 20g may be enhanced by several differing means. For example, empirical studies may show that the cell-scraping ability of said sharp edges is enhanced by making said sharp edges abrasive. A polymer or polymers of the type that cellular material clings to could be added to the sharp edge or edges. Adhesive of the type that cellular material clings to could also be added to said sharp edge or edges.

As drawn, the cut that forms sharp edges 20, 20a, 20b, and 20f is disposed substantially parallel to the bevel cut that forms first sharp edge 14 of needle 10. Accordingly, said sharp edges scrape tissue with the same degree of efficiency as first sharp edge 14. The scraping action provided by these sharp edges is during the distal-to-proximal stroke of needle 10 whereas the scraping action provided by first sharp edge 14 is during the proximal-to-distal stroke.

The cut that forms third sharp edges 20c, 20d, 20e, and 20g is substantially normal to the cut that forms second sharp edges 20, 20a, 20b, and 20f. The scraping action of said third sharp edges is during proximal-to-distal motion of the needle and as such said third sharp edges cut cellular material at the same time that first sharp edge 14 cuts cellular material.

In this way, a physician can reciprocate the needle along its longitudinal axis and obtain multiple cellular-sized samples of tissue for analysis.

Needle 10 is used by inserting it into a lesion in a well-known way and by reciprocating it multiple times along its longitudinal axis. Each proximal-to-distal displacement causes first sharp edge 14 and third sharp edges 20c, 20d, 20e, or 20g, depending upon the embodiment used, to sever cells from the lesion and a vacuum pulls such cellular aspirate of the lesion into lumen 16. Each distal-to-proximal motion, however, causes second sharp edges 20, 20a, 20b, or 20f, depending upon the embodiment used, to scrape off parts of the lesion. These scraped-off parts of the lesion enter into lumen 16 through slot 18, slot 18a, or channel 21, depending upon the embodiment in use, under the influence of the vacuum. Thus, in a single reciprocation, novel aspiration biopsy needle 10 collects at least twice the amount of lesion material as would a conventional aspiration biopsy needle. The quantity of scraped-off lesion parts collected is increased with each subsequent reciprocation. In this way, a sufficient sample may be taken with a single needle insertion followed by multiple reciprocations.

Additional quantities of lesion material may also be collected by rotating needle 10 about its longitudinal axis of symmetry after a first set of reciprocations has been made. Additional rotations may follow additional reciprocations, it being understood that each rotational adjustment exposes an unscraped mass of lesion until the needle has been through three hundred sixty degrees of rotation.

Figure 17:
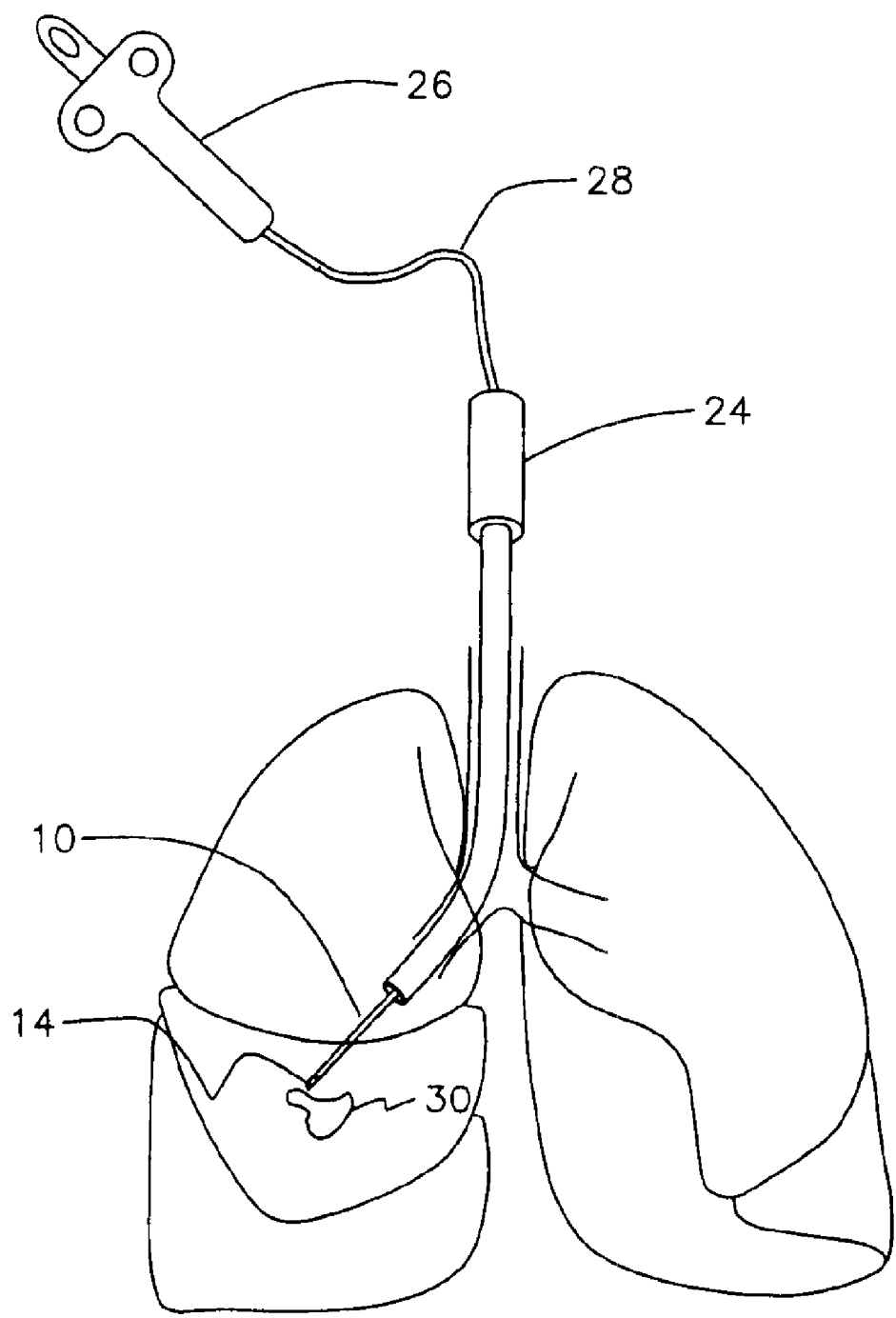
FIG. 17 is a diagrammatic view of a fourteenth embodiment where the novel biopsy device is used with an endoscope.

FIG. 17 depicts how an endoscope or laparoscope 24 is used in connection with fine needle aspiration biopsy device 10. The well-known attachments to the endoscope such as a light source, camera unit, monitor, and the like are not depicted to avoid cluttering the drawing. Syringe 26 is of conventional construction and is connected to an elongate, flexible polymer tube or a guide tube 28 of the hollow, coiled cable type. Tube wire 28 may be up to one hundred fifty centimeters (150 cm) in length and is inserted into the operating channel of the endoscope or laparoscope 24 as depicted. Novel fine aspiration biopsy device 10 is secured to the distal end of the tube or guide wire 28. Although it is difficult to push device 10 to retrieve cellular material from lesion 30 as in the earlier embodiments, it can be pulled to collect such cellular material because it cuts at the cellular level in both forward and rearward motions. Pulling of guide tube 28 results in rearward motion of device 10.

These improvements represent revolutionary improvements in the art of aspiration biopsy needles and this invention is therefore entitled to the status of a pioneering invention. Accordingly, the claims that follow are entitled to broad interpretation, as a matter of law, to protect the heart or essence of the invention.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An aspiration biopsy needle, comprising:

a needle of elongate, hollow construction having a proximal end and a beveled distal end;

said needle having a uniform diameter along its extent;

said beveled distal end forming a first sharp edge adapted to scrape cellular material when said needle is displaced from a proximal position to a distal position;

a first slot formed in said needle near said beveled distal end;

said first slot being transversely disposed relative to a longitudinal axis of said needle;

said first slot also being angled relative to a transverse axis of said needle such that a bottom of said first slot is positioned proximal to an opening of said first slot;

said opening of said first slot being in open communication with an exterior surface of said needle;

said first slot including a second sharp edge adapted to scrape cellular material when said needle is displaced from a proximal position to a distal position;

means for communicating a vacuum to said proximal end of said needle so that cellular material scraped by said first sharp edge during proximal-to-distal travel of said needle is pulled into a lumen of said needle and so that cellular material scraped by said second sharp edge during said proximal-to-distal travel of said needle is also pulled into said lumen;

said second sharp edge being elevated with respect to said exterior surface of said needle.

2. An aspiration biopsy needle, comprising:

a needle of elongate, hollow construction having a proximal end and a beveled distal end;

said needle having a uniform diameter along its extent;

said beveled distal end forming a first sharp edge adapted to scrape cellular material when said needle is displaced from a proximal position to a distal position;

a first slot formed in said needle near said beveled distal end;

said first slot being transversely disposed relative to a longitudinal axis of said needle;

said first slot also being angled relative to a transverse axis of said needle such that a bottom of said first slot is positioned proximal to an opening of said first slot;

said opening of said first slot being in open communication with an exterior surface of said needle;

said first slot including a second sharp edge adapted to scrape cellular material when said needle is displaced from a proximal position to a distal position;

means for communicating a vacuum to said proximal end of said needle so that cellular material scraped by said first sharp edge during proximal-to-distal travel of said needle is pulled into a lumen of said needle and so that cellular material scraped by said second sharp edge during said proximal-to-distal travel of said needle is also pulled into said lumen; and a hinge to which said second sharp edge is mounted to enable pivotal movement of said second sharp edge.

* * * * *